(12) United States Patent
Jenkins et al.

(10) Patent No.: US 9,658,193 B2
(45) Date of Patent: May 23, 2017

(54) ROLLING PHASED ARRAY ULTRASONIC SCANNER

(71) Applicant: General Electric Company, Schenectady, NY (US)

(72) Inventors: Thomas Richard Jenkins, Lewistown, PA (US); Dane Eugene Hackenberger, Mifflintown, PA (US); Robert Charles Shaffer, Reedsville, PA (US)

(73) Assignee: General Electric Company, Schenectady, NY (US)

( * ) Notice: Subject to any disclaimer, the term of this patent is extended or adjusted under 35 U.S.C. 154(b) by 353 days.

(21) Appl. No.: 14/024,095

(22) Filed: Sep. 11, 2013

(65) Prior Publication Data
US 2015/0068312 A1 Mar. 12, 2015

(51) Int. Cl.
G01N 29/26 (2006.01)
G01N 29/24 (2006.01)
G01N 29/04 (2006.01)
G01N 29/22 (2006.01)

(52) U.S. Cl.
CPC ......... G01N 29/262 (2013.01); G01N 29/221 (2013.01); G01N 29/2493 (2013.01)

(58) Field of Classification Search
CPC .. G01N 29/2493; G01N 29/28; G01N 29/265; G01N 29/043; G01N 29/2475
USPC ............. 73/638, 635, 636, 618, 639
See application file for complete search history.

(56) References Cited

U.S. PATENT DOCUMENTS

| 3,257,843 | A | * | 6/1966 | Cowan | ............... | G01N 29/2493 |
| | | | | | | 310/336 |
| 3,415,110 | A | * | 12/1968 | Cowan | ............... | G01N 29/0618 |
| | | | | | | 73/609 |
| 4,174,636 | A | * | 11/1979 | Pagano | ............... | G01N 29/043 |
| | | | | | | 73/636 |
| 4,217,782 | A | | 8/1980 | Pont | | |
| 5,027,820 | A | * | 7/1991 | Pesque | ............... | G01S 15/8929 |
| | | | | | | 128/916 |
| 5,228,343 | A | | 7/1993 | Schoenen et al. | | |
| 5,392,652 | A | * | 2/1995 | Levesque | ............. | G01N 29/043 |
| | | | | | | 73/629 |
| 5,419,196 | A | * | 5/1995 | Havira | ................ | G01N 29/221 |
| | | | | | | 73/623 |
| 5,485,751 | A | | 1/1996 | Karbach et al. | | |
| 5,549,004 | A | * | 8/1996 | Nugent | ............. | G01N 29/2487 |
| | | | | | | 376/249 |
| 6,604,421 | B1 | * | 8/2003 | Li | ............................ | B61K 9/10 |
| | | | | | | 73/636 |

(Continued)

FOREIGN PATENT DOCUMENTS

DE 10014936 C1 10/2001
WO 2012131334 A1 10/2012

OTHER PUBLICATIONS

PCT Search Report and Written Opinion issued in connection with corresponding Application No. PCT/US2014/055045 on Dec. 1, 2014.

Primary Examiner — Helen Kwok
(74) Attorney, Agent, or Firm — Barclay Damon, LLP

(57) ABSTRACT

A rolling ultrasonic scanner comprises a member having an inspection surface for rolling across the surface of an object under test. A plurality of ultrasonic transducers are disposed within the member in a formation such that they are each aimed at a common point that is coincident with the surface of the object.

20 Claims, 2 Drawing Sheets

(56) References Cited

U.S. PATENT DOCUMENTS

| | | | |
|---|---|---|---|
| 7,213,459 B2* | 5/2007 | Sengupta | G01N 29/043 73/636 |
| 9,247,926 B2* | 2/2016 | Smith | A61B 8/58 |
| 9,261,489 B2* | 2/2016 | Jones | G01N 29/226 |
| 2001/0032513 A1* | 10/2001 | Havira | B61K 9/10 73/636 |
| 2006/0065055 A1* | 3/2006 | Barshinger | B61K 9/10 73/609 |
| 2007/0068253 A1* | 3/2007 | Carodiskey | G01N 29/0618 73/570 |
| 2011/0100128 A1* | 5/2011 | Bond-Thorley | G01N 29/28 73/641 |
| 2012/0291555 A1* | 11/2012 | Hackenberger | G01N 29/2493 73/635 |
| 2012/0310551 A1* | 12/2012 | Na | G01N 29/0645 702/39 |
| 2013/0047729 A1 | 2/2013 | Wigh et al. | |
| 2013/0220019 A1* | 8/2013 | Havira | G01N 29/2493 73/636 |
| 2014/0007689 A1* | 1/2014 | Bond-Thorley | G01N 29/2493 73/618 |
| 2014/0095085 A1* | 4/2014 | Fetzer | G01N 29/043 702/56 |
| 2014/0150557 A1* | 6/2014 | De Miguel Giraldo | G01N 29/2493 73/635 |

* cited by examiner

ROLLING PHASED ARRAY ULTRASONIC SCANNER

BACKGROUND OF THE INVENTION

The subject matter disclosed herein relates to a phased array ultrasonic scanner and, in particular, to a rolling phased array ultrasonic scanner.

Nondestructive inspection devices can be used to inspect test objects and to detect and analyze anomalies, defects and characteristics therein. Nondestructive inspection allows a technician to maneuver a probe on or near the surface of the test object in order to perform testing of both the object surface and its underlying structure. One example of a nondestructive inspection apparatus is an ultrasonic scanner.

A rolling ultrasonic scanner is one type of scanner that is used to provide an image of an object or part to reveal flaws, defects, characteristics, or anomalies in the object. A rolling ultrasonic scanner includes a cylindrical rotating portion, or wheel, filled with an acoustically transmissive fluid such as water or propylene glycol. The fluid enables coupling of ultrasonic signals emitted by a transducer unit within the cylinder with the object being inspected. In many instances, the rolling ultrasonic scanner is a hand held apparatus that the user manually rolls across the object under test to produce data from the object.

In operation, electrical pulses are transmitted to the transducer unit. The transducer unit transforms the electrical pulses into ultrasonic waves using one or more ultrasonic transducers (e.g., piezoelectric elements) arranged in an array within the scanner. The ultrasonic waves generated by the transducers are transmitted into the test object to which the scanner is coupled. As the ultrasonic waves pass into the test object, various reflections, called echoes, occur as the ultrasonic waves interact with anomalies and other physical characteristics in the test object. Conversely, when the reflected ultrasonic waves are received by the piezoelectric surface of the ultrasonic transducers, it causes the transducers to vibrate which generates a voltage difference across the transducer electrodes that is detected as an electrical signal by signal processing electronics connected to the transducers through the cable. The signal processing circuits track the time difference between the transmission of the electrical pulses and the receipt of the electrical signals, and measure the amplitude of the received electrical signals to determine various attributes of any anomalies and characteristics of the object, such as depth, size, location, and orientation.

A phased linear array ultrasonic scanner has a plurality of electrically and acoustically independent ultrasonic transducers in a single linear array. By varying the timing of the electrical pulses applied to the ultrasonic transducers using delay criteria, a phased linear array ultrasonic probe can generate ultrasonic waves passing into the test object at different angles (e.g., from zero to one hundred eighty degrees) to try to detect anomalies and variances therein and to identify the orientation of those anomalies and variances. For example, to generate an ultrasonic wave at thirty degrees, the transmit delays for the ultrasonic transducers of the phased array ultrasonic probe can be set in a first configuration of values. To then generate an ultrasonic wave at thirty-two degrees, for example, the transmit delays for the ultrasonic transducers of the phased array ultrasonic probe can be set in a second configuration of values. This sequential generation, transmission, and receipt of the ultrasonic waves at each of the different angles is quite time consuming and results in a longer inspection time of the test object, especially if a one hundred eighty degree scan is required at different locations on the test object. While a linear scan provides efficient detection of corrosion or delamination, for example, those flaws are typically parallel to the entry point, i.e., where the ultrasonic waves enter the test object. Therefore, flaws oriented at different unknown angles require a time consuming procedure to insure that they are detected.

The discussion above is merely provided for general background information and is not intended to be used as an aid in determining the scope of the claimed subject matter.

BRIEF DESCRIPTION OF THE INVENTION

A rolling ultrasonic scanner comprises a cylinder having an inspection surface for rolling across the surface of an object under test. A plurality of ultrasonic transducers are disposed within the cylinder in a curved formation such that they are each aimed at a common point that is coincident with the surface of the object under test. An advantage that is realized in the practice of some disclosed embodiments is the capability to perform sectoral scans of a test specimen, instead of only linear scans, due to the transducers in the array each emitting an ultrasonic beam toward the test specimen at a different angle.

In one embodiment, an ultrasonic scanner includes a member having an inspection surface for rolling across a surface of an object to be inspected. An axle is attached to the member wherein the member moves relative to the axle during an inspection. A plurality of ultrasonic transducers are fixed within the member in a formation such that they are aimed at a common point on the surface of the object to be inspected.

In another embodiment, an ultrasonic scanner includes a cylinder having an inside surface and an outside surface. A pair of end caps, one at each end of the cylinder, enclose an interior of the cylinder. An axle extends through the pair of end caps and through the interior of the cylinder. An array of ultrasonic transducers is disposed in a housing within the interior of the cylinder so that they all can be aimed at a common exit point coincident with the outside surface of the cylinder.

In another embodiment, an apparatus includes a phased array of ultrasonic transducers, and a housing for fixing the transducers in a formation such that transducers are each aimed at a common point. A wheel comprises a hollow interior within which the housing and the ultrasonic transducers are disposed, and wherein said common point is coincident with an exterior surface of the wheel.

This brief description of the invention is intended only to provide a brief overview of subject matter disclosed herein according to one or more illustrative embodiments, and does not serve as a guide to interpreting the claims or to define or limit the scope of the invention, which is defined only by the appended claims. This brief description is provided to introduce an illustrative selection of concepts in a simplified form that are further described below in the detailed description. This brief description is not intended to identify key features or essential features of the claimed subject matter, nor is it intended to be used as an aid in determining the scope of the claimed subject matter. The claimed subject matter is not limited to implementations that solve any or all disadvantages noted in the background.

BRIEF DESCRIPTION OF THE DRAWINGS

So that the manner in which the features of the invention can be understood, a detailed description of the invention may be had by reference to certain embodiments, some of which are illustrated in the accompanying drawings. It is to be noted, however, that the drawings illustrate only certain embodiments of this invention and are therefore not to be considered limiting of its scope, for the scope of the invention encompasses other equally effective embodiments. The drawings are not necessarily to scale, emphasis generally being placed upon illustrating the features of certain embodiments of the invention. In the drawings, like numerals are used to indicate like parts throughout the various views. Thus, for further understanding of the invention, reference can be made to the following detailed description, read in connection with the drawings in which.

DETAILED DESCRIPTION OF THE INVENTION

Figure 1:
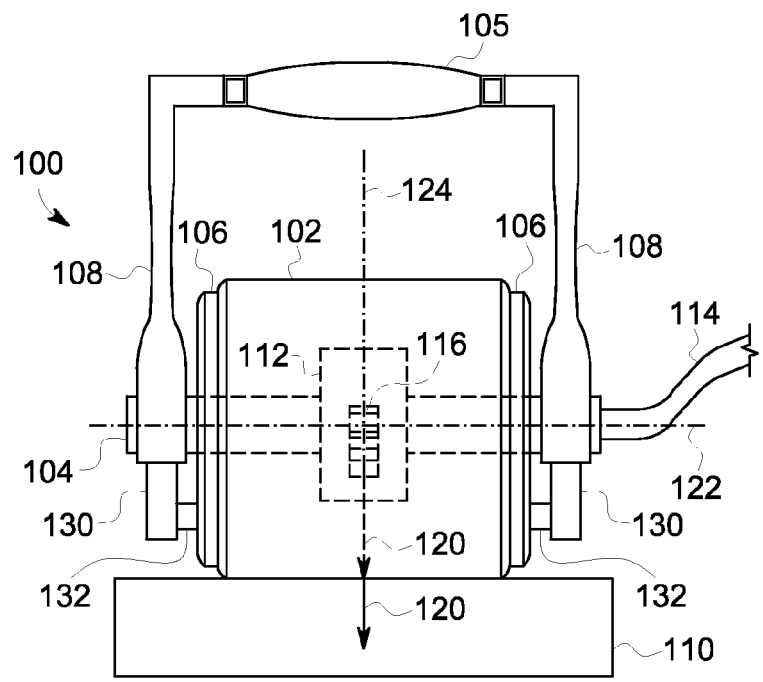
FIG. 1 is a front view diagram of an exemplary embodiment of a curved phased array rolling ultrasonic scanner.
Figure 2:
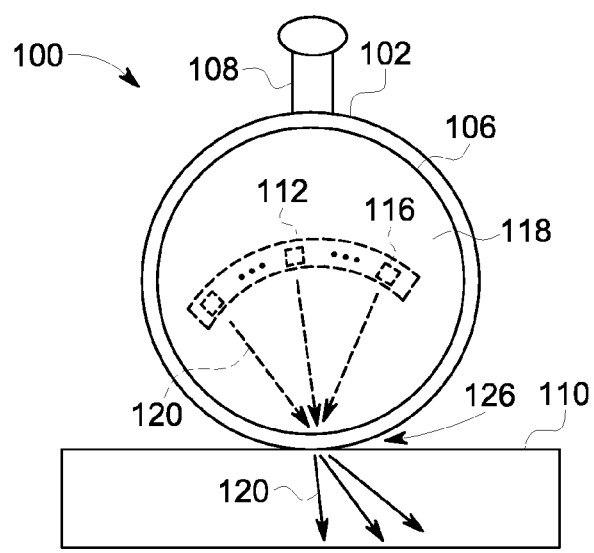
FIG. 2 is a partial cutaway side view diagram of the exemplary curved phased array rolling ultrasonic scanner of FIG. 1.

FIGS. 1 and 2 illustrate one embodiment of an exemplary rolling ultrasonic scanner 100. The rolling ultrasonic scanner 100 includes a cylindrical member 102 having two opposed ends that are mounted to end caps, or discs, 106. The end caps, in turn, are rotatably attached to a non-rotating axle 104, thereby allowing relative rotation of the cylindrical member 102 and end caps 106 about the axle 104. The cylindrical member 102 and the end caps 106 together define an interior, substantially cylindrical, region 118 (FIG. 2) of the rotating portion of the rolling ultrasonic scanner 100.

The cylindrical member 102 has a thickness of one to several millimeters and has an outside facing cylindrical surface having an outside diameter and an inside facing cylindrical surface having an inside diameter. The axle 104 is configured to be rotatably coupled to the end caps 106 and fixed to frame members 108. The frame members 108, in turn, are together attached to, or include, a handle 105 for manually rolling and manipulating the rolling ultrasonic scanner 100 over the surface of an object or test piece 110 to be inspected. The frame members 108 are made from any suitable rigid material such as a metal or plastic. As will be explained in more detail below with regard to FIG. 3, the frame members 108 are attached to support frame members 130 which, in turn, are rotatably attached to a secondary axle 132.

Exemplary frame members 108 include electronics hardware attached thereto (not shown), such as an encoder, to transmit coded electrical pulses to the transducer unit 112 for generating corresponding ultrasonic waves during ultrasonic scanning operations. The electronics are coupled to an external electronic display and to a processing system via an electrical cable 114 disposed at least partially within axle 104. The display presents scanned images of the object under inspection 110 and the processing system (not shown) analyzes and stores the scan data. In one embodiment, the axle 104 is coupled to the end caps 106 via a bearing assembly to allow the cylindrical member 102 and the end caps 106 to rotate together, or roll, as a single unit.

The rolling ultrasonic scanner 100 includes a transducer unit 112 within the interior region 118 which, in one embodiment, includes a housing enclosing a plurality of ultrasonic transducer elements 116. The number of transducer elements 116 within the transducer unit 112 include sixty four or one hundred twenty eight transducer elements. The number of transducer elements enclosed by the housing 112 is not considered to be a limiting factor in the embodiments disclosed herein. The ultrasonic transducer elements 116 are fixed in the housing and are arranged in a curved formation, with associated hardware and circuitry, configured to emit ultrasonic waves, or beams, and to detect echoes thereof. As used herein, the terms ultrasonic wave and ultrasonic beam are considered to be synonymous and interchangeable.

The transducer housing 112 is attached to the axle 104. The plurality of transducer elements 116 within the housing do not rotate with the cylindrical member 102 and the end caps 106. The transducer housing 112 need not be attached in a concentric relation to the axle 104, and can be attached or mounted to the axle using bolts, for example. The ultrasonic transducer elements 116 are also connected to the signal processing electronics, or processing system, via the cable 114. The echoes provide information about the condition or character of the object under inspection 110. In the rolling ultrasonic scanner 100, the processing system coupled to the rolling ultrasonic scanner 100 via cable 114 is configured to send, receive and process signals corresponding to the emitted ultrasonic waves 120. Software and/or firmware runs on the signal processing electronics, or processing system, to analyze the waves and to determine if there are imperfections or anomalies in the object under inspection 110. By transmitting an ultrasonic wave 120 of known characteristics (i.e., frequency, amplitude, etc.) into the object under inspection 110, anomalies in the object under inspection 110 can be determined by analyzing characteristics of the echoes.

An acoustically transmissive fluid fills the interior region 118 and serves to acoustically couple the transducer elements 116 in the transducer unit 112 to the object under inspection 110 for transmitting ultrasonic waves 120 into the object under inspection 110 and receiving echoes of the ultrasonic waves therefrom. The fluid includes water or propylene glycol, for example. In one embodiment, the cylindrical member 102 comprises a substantially flexible elastomeric material, rubber, or polymer, or a combination thereof, that is expanded, or stretched, over end caps 106. The fluid within the interior region 118 is pumped therein under an amount of pressure such that the flexible cylindrical member 102 bows slightly outward. The cylindrical member 102 thereby provides a flexible and conformable inspection surface that used to manually roll over and efficiently scan objects having uneven or non-flat surfaces. The conformable material thereby allows the inspection surface to maintain contact with uneven surface features of the object under test 110, such as weld beads. This flexible cylindrical member 102 is often referred to as a tire or a wheel, because it is similar in certain respects to tires or wheels on a vehicle rolling on a paved roadway, for example, wherein a contact region is created when the flexible cylindrical member 102 rolls over the surface of the object to be inspected 110. The contact region provides a common surface area with the object under inspection 110 through which the ultrasonic waves 120 are transmitted into the object 110. The fluid within the interior region 118 of the rolling ultrasonic scanner 100 and the contact region defines a transmission path for the ultrasonic waves 120 with minimal distortion.

FIG. 2 depicts a partial side view of the rolling ultrasonic transducer 100 with some components not shown for ease of illustration and clarity in the Figure. As illustrated in FIG. 2, the transducer unit 112 includes a phased array of ultrasonic transducers 116 arranged in a curved formation to transmit ultrasonic beams 120 in a coded sequence or pattern and to receive echoes generated by the transmitted beams 120. The ultrasonic beams 120 are transmitted toward a common exit point 126 coincident with a surface of the object under test 110, which is substantially identical to the outside surface of the cylindrical member 102. As illustrated in FIG. 1, the transducer elements 116 of the transducer unit 112 are disposed along an axis 124 substantially perpendicular to a longitudinal axis 122 of the cylindrical member 102. It will be understood that the orientation of the transducer elements 116 of the transducer unit 112 is not limited to the exemplary embodiments illustrated herein, and are oriented in a different angular relationship, in one or more dimensions, to the longitudinal axis 122. By transmitting ultrasonic beams into the test object 110 at several angles simultaneously, as shown in FIG. 2, flaws and defects oriented at various angles can be detected.

For example, cracks and other defects that radiate perpendicular to the surface require a controllable sector scan in order to be detected, which is enabled by the converging ultrasonic beams 120 provided by the phased array rolling ultrasonic scanner disclosed herein. Some of the beams 120 enter the object under inspection 110 at various angles. The curved array of transducer elements 116 allows the inspection of multiple angles due to each of transducer elements 116 focused at the common exit point 120 and firing a different group of transducer elements 116 to produce the various angles required for the inspection. By firing different groups of transducer elements 116 instead of steering the elements (required for flat or linear array) there is less sensitivity loss and the ability to maintain a constant common exit point 126 is created between the rolling ultrasonic scanner 100 and the object under inspection 110. Some of the beams enter the object under inspection 110 at a high angle and are able to scan the entire volume of the object under inspection 110 due to the high acoustic velocity difference between the fluid within the interior region 118 and the object under inspection 110. This improves the ability to better steer the ultrasonic beams 120 within the constraints of being aimed at the common exit point 126 where the ultrasonic beams 120 converge. For example, to propagate an ultrasonic beam at 30° in the object under inspection 110, which is typically performed during inspection, embodiments disclosed herein require that an ultrasonic beam be steered 15° from the transducer elements, because the velocity ratio as between the acoustically transmissive fluid in the interior region 118 and the object under test provides a 2× velocity ratio. The higher acoustic velocity ratio enables reaching those limits more easily.

Figure 3:
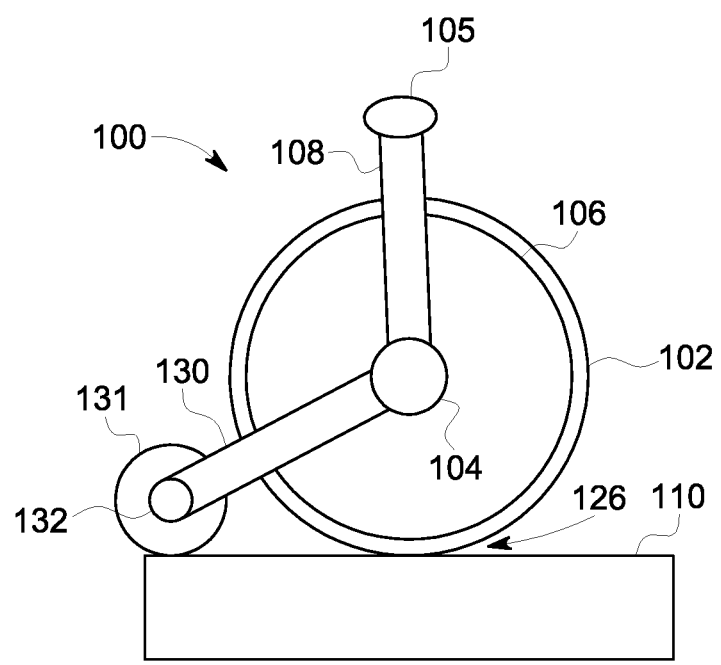
FIG. 3 is a side view diagram of the exemplary curved phased array rolling ultrasonic scanner illustrating the support frame members and support wheel.

FIG. 3 illustrates a side view of the rolling ultrasonic scanner 100 having support frame members 130 attached thereto. Each support frame member 130 is attached at one end at a fixed angle to one of the frame members 108. The other ends of the support frame members 130 are fixed to a secondary axle 132. The secondary axle comprises at least one support wheel 131 rotatably attached to the secondary axle 132, such as by roller bearings. Thus, the handle 105, frame members 108, support frame members 130, secondary axle 132, axle 104 and the transducer unit 112 attached thereto form a substantially rigid assembly that secures these components in a fixed spatial relationship to each other. The cylindrical member 102 and end caps 106 are configured to rotate in relation to this assembly. In operation, as the cylindrical member 102 rolls over an object under inspection 110, the support wheel 131, in conjunction with the secondary axle 132 and the support frame members 130, maintains the transducer unit 112 at a fixed angle with respect to the common exit point 126. Thus, the ultrasonic waves 120 emitted by the transducer elements 116 are consistently aimed at the common exit point 126 during operation.

In view of the foregoing, embodiments of the invention provide a scanning capability enabling high angle transmission that was previously achieved using, for example, a wedge made of plastic or other material that inserted between the scanner and the object under test. The curved array of transducer elements 116 achieves this with the fluid filled interior region 118 because it uses the location of the transducer elements 116 to create the angularity of the ultrasonic beam 120 instead of electrically steering the ultrasonic beam 120 to create the angularity of the beam. The higher acoustic velocity ratio allows smaller element spacing in order to achieve the higher range of scanning angles. The fluid filled interior region 118 achieves this because of the higher acoustic velocity ratio as between the fluid and the object under test compared with an intervening wedge piece and the object under test. Thus, a higher range of scanning angles is enabled and the transducer elements themselves are arranged in a tighter pitch which requires less space within the cylindrical member 102. Another advantage of using the fluid filled cylindrical member 102, as disclosed herein, is that the fluid imposes less attenuation of the ultrasonic waves generated by the transducer elements 116 than does a solid wedge piece.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:
1. An ultrasonic scanner comprising:
a member having an inspection surface for rolling across a surface of an object to be inspected;
an axle attached to the member wherein the member moves relative to the axle during said rolling across the surface of the object to be inspected;
a curved transducer housing unit disposed within the member, the curved transducer housing unit being spaced apart from and mounted in transverse relation to the axle, wherein a curvature of the curved transducer housing unit is configured to focus on a common point on the surface of the object to be inspected;
electronics hardware disposed within the member, the electronics hardware comprising at least an encoder;
a plurality of ultrasonic transducers disposed within the member, the plurality of ultrasonic transducers including at least sixty four ultrasonic transducers, wherein the plurality of ultrasonic transducers are fixed in a curved formation on the curved transducer housing unit such that the plurality of ultrasonic transducers are each aimed at the common point on the surface of the object to be inspected, the curved formation of the plurality of ultrasonic transducers on the curved transducer housing unit facilitating focusing of the plurality of ultrasonic transducers on the common point on the surface of the object, wherein the plurality of ultrasonic transducers comprises a phased array of ultrasonic transducers, and the ultrasonic scanner is configured to activate a first group of the plurality of ultrasonic transducers to inspect at a first inspection angle and a second group of the plurality of ultrasonic transducers to inspect at a second inspection angle, the first group and second group being different groups, wherein activating the different groups of ultrasonic transducers mitigates sensitivity loss of the ultrasonic scanner during inspection of the object; and
a signal processing electrical cable, the signal processing electrical cable being electrically coupled to the plurality of ultrasonic transducers and disposed at least partially within the axle.

2. The ultrasonic scanner of claim 1, wherein the member is filled with an acoustically transmissive fluid.

3. The ultrasonic scanner of claim 2, wherein the acoustically transmissive fluid is under a pressure such that the inspection surface of the member bows outward relative to the axle.

4. The ultrasonic scanner of claim 2, wherein the member comprises a cylindrical shape.

5. The ultrasonic scanner of claim 1, further comprising a transducer housing for fixing the plurality of ultrasonic transducers in the curved formation, the transducer housing being attached to the axle.

6. The ultrasonic scanner of claim 1, wherein the member comprises a flexible material that conforms to the surface of the object to be inspected.

7. The ultrasonic scanner of claim 1, further comprising a frame connected to the axle, wherein the frame comprises a handle for a user to grasp while rolling the ultrasonic scanner across the object to be inspected.

8. The ultrasonic scanner of claim 1, wherein the plurality of ultrasonic transducers are aligned along an axis perpendicular to a longitudinal axis of the member.

9. The ultrasonic scanner of claim 1, further comprising end caps attached to the axle, wherein the member is attached to the end caps at two opposite ends of the member.

10. An ultrasonic scanner comprising:
a cylinder having an inside surface and an outside surface;
a pair of end caps, one end cap of the pair of end caps being at each end of the cylinder for enclosing an interior of the cylinder;
an axle extending through the pair of end caps and through the interior of the cylinder;
a curved transducer housing unit disposed within the cylinder, the curved transducer housing unit being spaced apart from and mounted in transverse relation to the axle, wherein a curvature of the curved transducer housing unit is configured to focus on a common point on a surface of an object to be inspected;
electronics hardware disposed within the cylinder, the electronics hardware comprising at least an encoder;
an array of ultrasonic transducers disposed in a curved formation on the curved transducer housing unit within the interior of the cylinder, the array of ultrasonic transducers including at least sixty four ultrasonic transducers, wherein the curved transducer housing unit is attached to the axle, wherein each of the ultrasonic transducers is aimed at the common point coincident with the outside surface of the cylinder, wherein the curved formation of the array of ultrasonic transducers on the curved transducer housing unit and the disposition of the array of ultrasonic transducers in the curved transducer housing unit facilitate focusing of the array of ultrasonic transducers on the common point on the outside surface of the cylinder, wherein the array of ultrasonic transducers comprises a phased array of ultrasonic transducers, and wherein the ultrasonic scanner is configured to activate a first group of the phased array of ultrasonic transducers to inspect at a first inspection angle and a second group of the phased array of ultrasonic transducers to inspect at a second inspection angle, the first group and second group being different groups, wherein activating the different groups of ultrasonic transducers mitigates sensitivity loss of the ultrasonic scanner during inspection of an object disposed adjacent to the outside surface of the cylinder; and
a signal processing electrical cable, the signal processing electrical cable being electrically coupled to the phased array of ultrasonic transducers and disposed at least partially within the axle.

11. The ultrasonic scanner of claim 10, wherein the array of ultrasonic transducers is aligned perpendicularly to an axis of the cylinder.

12. The ultrasonic scanner of claim 10, wherein the interior of the cylinder is filled with an acoustically transmissive fluid.

13. The ultrasonic scanner of claim 12, wherein the acoustically transmissive fluid is under a pressure such that the outside surface of the cylinder bows outward relative to the axle.

14. The ultrasonic scanner of claim 12 wherein the ultrasonic scanner is configured to manually roll the outside surface of the cylinder over the object to be inspected and to transmit ultrasonic beams generated by the array of ultrasonic transducers into the object to be inspected.

15. The ultrasonic scanner of claim 12 wherein the cylinder comprises an elastomeric material, a rubber material, a polymer material, or a combination thereof.

16. The ultrasonic scanner of claim 14, further comprising a handle attached to the axle for a user to grasp and manually roll the outside surface of the cylinder over the object to be inspected.

17. An apparatus comprising:
a phased array of ultrasonic transducers, the phased array of ultrasonic transducers including at least sixty four ultrasonic transducers;
a curved transducer housing unit, wherein the phased array of ultrasonic transducers is fixed in a curved formation within the curved transducer housing unit, wherein each of the transducers is aimed at a common point, wherein the curved formation facilitates focusing of the phased array of ultrasonic transducers on the common point on, and wherein the apparatus is configured to activate a first group of the phased array of ultrasonic transducers to inspect at a first inspection angle and a second group of the phased array of ultrasonic transducers to inspect at a second inspection angle, the first group and second group being different groups, wherein activating the different groups of ultrasonic transducers mitigates sensitivity loss during inspection of an object disposed at the common point;
a wheel comprising a hollow interior within which the curved transducer housing unit having the phased array of ultrasonic transducers is disposed, and wherein said common point is coincident with an exterior surface of the wheel;
an axle attached to the wheel, wherein the curved transducer housing unit is spaced apart from and mounted in transverse relation to the axle;

electronics hardware disposed within the hollow interior of the wheel, the electronics hardware comprising at least an encoder; and a signal processing electrical cable, the signal processing electrical cable being electrically coupled to the phased array of ultrasonic transducers and being disposed at least partially within the axle.

18. The apparatus of claim 17, wherein said hollow interior of the wheel is filled with an acoustically transmissive fluid.

19. The apparatus of claim 18, wherein the acoustically transmissive fluid is selected such that an acoustic velocity ratio as between the object to be inspected and the acoustically transmissive fluid is equal to or greater than about two.

20. The apparatus of claim 18, further comprising a handle attached to the axle for being grasped by a user to roll the apparatus over the object to be inspected.

\* \* \* \* \*